United States Patent [19]

Matsuura et al.

[11] Patent Number: 5,756,088
[45] Date of Patent: May 26, 1998

[54] PRESCRIPTION DIET COMPOSITION FOR TREATMENT OF DOG AND CAT DERMATOSIS

[75] Inventors: Ichiro Matsuura, Tokyo; Toshizumi Saito, Musashimurayama; Kenjiro Shimada, Tsuchiura, all of Japan

[73] Assignee: Kyowa Hakko Kogyo Co., Ltd., Tokyo, Japan

[21] Appl. No.: 532,389

[22] Filed: Sep. 22, 1995

Related U.S. Application Data

[63] Continuation of Ser. No. 186,549, Jan. 26, 1994, abandoned.

[30] Foreign Application Priority Data

Jan. 27, 1993 [JP] Japan .................. 5-011984

[51] Int. Cl.$^6$ .................. A01N 63/02
[52] U.S. Cl. ........... 424/93.4; 424/93.1; 424/93.41; 424/93.44; 424/93.45; 424/93.46; 424/439; 424/442; 426/2; 426/61
[58] Field of Search .................. 424/93.1, 93.4, 424/93.41, 93.44, 439, 442, 93.46, 93.45; 426/2, 805; 514/861

[56] References Cited

U.S. PATENT DOCUMENTS

| | | | |
|---|---|---|---|
| 3,857,971 | 12/1974 | Abdo et al. | 426/53 |
| 4,147,773 | 4/1979 | Ogasa | 424/93 |
| 4,820,529 | 4/1989 | Uchida et al. | 426/7 |
| 4,963,370 | 10/1990 | Uchida et al. | 426/7 |
| 5,047,249 | 9/1991 | Rothman et al. | 424/543 |
| 5,066,498 | 11/1991 | McCauley, III | 426/2 |
| 5,202,136 | 4/1993 | Evans et al. | 426/2 |
| 5,244,669 | 9/1993 | Satoh et al. | 424/438 |
| 5,260,279 | 11/1993 | Greenberg | 514/21 |
| 5,549,729 | 8/1996 | Yamashita | 71/26 |

FOREIGN PATENT DOCUMENTS

| | | |
|---|---|---|
| 0241097 | 10/1987 | European Pat. Off. . |
| 2508282 | 12/1982 | France . |
| 1503094 | 3/1978 | United Kingdom . |

OTHER PUBLICATIONS

Nguyen et al., Reucueil De Medecine Veterinaire, vol. 165 (6–7) pp. 651–664 (1989).

Fromageot et al., Receuil Se Medecine Veterinaire, vol. 158 (12) pp. 821–826 (1982).

Fromageot et al., Recueil De Medecine Veterinaire, vol. 166 (2), pp. 87–94 (1990).

*The Merck Index*, 11th edition, Merck & Co., Inc., Bahway, N.J., 1989, p. 867.

Mock, D.M. et al., "The J. of Pediatics," vol. 106 (5), May 1985, pp. 762–769.

*Primary Examiner*—Chhaya D. Sayala
*Attorney, Agent, or Firm*—Antonelli, Terry, Stout & Kraus, LLP

[57] ABSTRACT

The present invention provides a prescription diet composition containing a poly-unsaturated fatty acid such as γ-linolenic acid, α-linolenic acid and docosahexaenoic acid, and/or biotin, and an antiflatulent such as a lactic acid bacterium, a Bifidbacterium, a butyric acid bacterium or a Bacillus. The prescription diet composition is useful for the prevention and treatment of dog and cat dermatosis.

8 Claims, No Drawings

5,756,088

PRESCRIPTION DIET COMPOSITION FOR TREATMENT OF DOG AND CAT DERMATOSIS

This application is a continuation application of Ser. No. 08/186,549 filed Jan. 26, 1994, now abandoned.

BACKGROUND OF THE INVENTION

The present invention relates to a prescription diet composition having prophylactic and therapeutic effects against dermatosis of pet animals.

Recently, along with longer life spans of pet animals as a result of improvement in veterinary medicine and the trend toward Europeanization of pet food, as well as the unnatural breeding environment of pet animals without regard to their nature, increase in the incidence of adult diseases and diseases caused by metabolism disorders of pet animals has increased.

Among these diseases, dermatosis is outwardly observable. Dermatosis easily becomes chronic, and often requires long-term treatment.

The treatment of dermatosis usually involves intramuscular or subcutaneous injection, oral administration or external application of antibacterial agents, steroids and the like. However, dermatosis is usually difficult to cure in a short period of time with the drugs alone. Moreover, long-term administration of the drugs often results in occurrence of side effects such as secondary adrenal cortical hypofunction, gastrointestinal disorders such as ulcers and bleeding, nephrotoxicity and chill of the infection.

It is known that since deficiency of essential fatty acids and biotin is the main cause of canine dermatosis, incorporation of such ingredients into pet foods is effective against canine dermatosis [Fromageot, D. et al., Rec. Med. Vet. 158, (12), 821–826, 1982]. Also, in cats a severe deficiency of Δ-6-desaturase inhibits the conversion of linolic acid into γ-linolenic acid, and incorporation of γ-linolenic acid into pet foods is known (Japanese Published Unexamined Patent Application No. 149054/86). Furthermore, the activity of Δ-6-desaturase in dogs is clearly attenuated by aging and diseases such as hepatic diseases and diabetes (Wolter, R. R., Wolter's Canine and Feline Nutrition Science, p.71, published by Nihon Rinsho Co., 1991), and thus the incorporation of poly-unsaturated fatty acids such as dihomo γ-linolenic acid, arachidonic acid, eicosapentaenoic acid, γ-linolenic acid and the like into canine and feline pet foods is known (Japanese Published Unexamined Patent Application No. 215245/89). Nevertheless, the effect of such pet foods is not yet satisfactory from the point of view of the prophylactic or therapeutic treatment of canine and feline dermatosis.

The use of antiflatulents for the purpose of prevention and treatment of diarrhea and loose passage is known (Japanese Published Unexamined Patent Application No. 118827/76, etc.), but their use for the purpose of prophylactic or therapeutic treatment of pet dermatosis is not known.

SUMMARY OF THE INVENTION

An object of the invention is to provide a prescription diet composition for pet animals, which comprises an antiflatulent; and at least one of poly-unsaturated fatty acid and biotin. Another object of the present invention is to provide a method for prophylactic or therapeutic treatment of dermatosis in a pet animal which comprises having the pet animal ingest the prescription diet composition.

DETAILED DESCRIPTION OF THE INVENTION

The poly-unsaturated fatty acid to be contained in the prescription diet composition of the present invention includes, for example, an ω3- or ω6-type essential fatty acid. Particularly preferred are γ-linolenic acid, α-linolenic acid, eicosapentaenoic acid, docosahexaenoic acid (hereinafter referred to as DHA), etc. The γ-linolenic acid, α-linolenic acid, eicosapentaenoic acid and DHA, etc. may be originated from any source. Specifically, the γ-linolenic acid may be derived from evening primrose oil, a microorganism belonging to the genus Mortierella or Mucor, an algae belonging to the genus Euglena or Chlorella, or from extracts thereof. The α-linolenic acid may be derived from seeds of plants such as *Perilla ocimoidis* var., *Perilla crispa ocimoidis*, L., Lineseed, rape seeds, soybean, etc. or from extracted oils thereof. The eicosapentaenoic acid and DHA may be derived from the oils of fishes such as sardines, bonito and tuna, from a microorganism belonging to the genus Mortierella, etc. or from extracted fluids thereof. The poly-unsaturated fatty acid to be contained in the prescription diet composition of the present invention may be in a free form or in the form of a salt or ester. The salt may be a non-toxic metal salt, for example, sodium salt, potassium salt and calcium salt, and the ester includes, for example, methyl ester, ethyl ester or the like.

The biotin, or vitamin H, to be contained in the prescription diet composition of the present invention may be either synthesized or extracted from a yeast, a microorganism belonging to the genus Bacillus, Escherichia or Corynebacterium, a plant, an animal organ, or a Chinese herbal medicine such as jumi-haidokuto, shofusan and toki-inshi.

The antiflatulent to be contained in the prescription diet composition of the present invention comprises materials having an action of suppressing the growth of harmful intestinal bacteria and/or of accelerating the growth of beneficial intestinal bacteria. For example, cells of a bacterium selected from lactic acid bacteria such as *Lactobacillus acidophilus*, *Streptococcus faecalis*, *Lactobacillus bulgaricus*, *Lactobacillus casei*, etc.; Bifidobacterium such as *Bifidobacterium bifidum*, *Bifidobacterium longum*, *Bifidobacterium breve*, *Bifidobacterium adolescentis*, *Bifidobacterium pseudolongum*, *Bifidobacterium thermophilum*, etc.; butyric acid bacteria such as *Clostridium butyricum*, etc.; Bacillus such as *Bacillus natto*, *Bacillus cereba toyoi*, and the like, as well as treated cells of the bacterium are mentioned. The treated cells include, for example, washed cells, dry cells, freezed cells, freeze-dried cells, acetone-dried cells, organic solvent-treated cells, surfactant-treated cells, lysozyme-treated cells, ultrasonically treated cells, mechanically disrupted cells, or the like.

The pet animals which may ingest the prescription diet composition of the present invention include small domestic animals such as dogs and cats.

The concentration of the poly-unsaturated fatty acid in the prescription diet composition of the present invention is 0.5–50 wt %, preferably 1–25 wt %. The concentration of the biotin is 0.01–1.0 wt %, preferably 0.04–0.4 wt %. The concentration of the antiflatulent is $10^6$–$10^{10}$ cells/per gram of the prescription diet composition (0.00001 to 10 wt % when calculated as dry cell weight).

In addition to the above-mentioned active ingredients, inactive auxiliary agents may be contained in the prescription diet composition. In order to enhance the effect of the antiflatulent, oligosaccharides such as fructooligosaccharide, soybean oligosaccharide, xylooligosaccharide, inulooligosaccharide and lactulose may be added. Also, amino acids such as methionine and taurine; vitamins such as vitamin A, vitamin $B_2$, vitamin $B_6$ and nicotinic acid; and zinc, which are known to be effective in treating dermatosis, may be added. Furthermore, for a nutritional standpoint, yeast extract, dry milk, proteins, enzymes, inorganic substances such as calcium, magnesium and phosphorus, nucleic acids, and essential fatty acids such as linolic acid may be added. For good taste, salts such as sodium chloride, organic acids and sweeteners such as sugar may be added; for the purpose of formulation of the prescription diet composition, emulsifiers such as enzymolytic lecithin, excipients such as lactose, cyclodextrin, grains, starch and calcium carbonate may be added; and for stability during transportation and storage, antioxidants such as vitamin E, β-carotene, vitamin C and lecithin may be added.

The concentration of these inactive ingredients in the prescription diet composition of the present invention is 0–99.99 wt %, preferably 5–95 wt %.

The prescription diet composition of the present invention may be used in combination with dermatotherapeutic medicines such as antibacterial agents (e.g. lincomycin), antipruritic agents (e.g. prednisolone), analgesics (e.g. salicylic acid), antiinflammatory agents (e.g. prednisolone), antiallergic agents (e.g. hydramine) and adrenal cortical hormone preparations (e.g. prednisolone), for the purpose of heightening the therapeutic effects of these medicines.

The prescription diet composition of the present invention may be ingested by a pet animal in the form of a powder, granules, pellets, tablets, a paste, an aqueous solution, or the like, either alone or as a mixture with feeds for pet animals.

The amount of intake of the prescription diet composition of the present invention per animal per day is preferably 0.1 g–2.5 g for pet animals having a body weight of less than 5 kg, 0.2 g–5.0 g for pet animals having a body weight of 5 kg or between 5 and 10 kg, 0.3 g–7.5 g for pet animals having a body weight of 10 kg or between 10 and 15 kg, and 0.5 g–20 g for pet animals having a body weight of 15 kg or above. The number of intake times is not particularly restricted, so long as the desired effect is manifested, but the daily intake times are preferably divided into two or more aliquots.

Examples of daily intake amounts of the prescription diet composition of the present invention are given below.

Pet animals having a body weight of less than 5 kg

| γ-linolenic acid | 4–250 mg |
|---|---|
| Biotin | 0.05–10 mg |
| Bifidobacterium | 0.1 μg–100 mg as dry cell weight ($10^6$–$10^{10}$ cells per gram of the composition) |

Pet animals having a body weight of 5 kg or between 5 and 10 kg.

| γ-linolenic acid | 8–500 mg |
|---|---|
| Biotin | 0.1–20 mg |
| Bifidobacterium | 0.1 μg–100 mg as dry cell weight ($10^6$–$10^{10}$ cells per gram of the composition) |

Pet animals having a body weight of 10 kg or between 10 and 15 kg.

| γ-linolenic acid | 12–750 mg |
|---|---|
| Biotin | 0.15–26 mg |
| Bifidobacterium | 0.1 μg–100 mg as dry cell weight ($10^6$–$10^{10}$ cells per gram of the composition) |

Pet animals having a body weight of 15 kg or above

| γ-linolenic acid | 20–2,000 mg |
|---|---|
| Biotin | 0.25–32 mg |
| Bifidobacterium | 0.1 μg–100 mg as dry cell weight ($10^6$–$10^{10}$ cells per gram of the composition) |

Prophylactic and therapeutic effects against pet dermatosis are produced by having pet animals ingest the prescription diet composition of the present invention.

The mechanism of the prophylactic and therapeutic effect is not completely clarified. It is considered that since the intestinal bacterial flora is improved by the antiflatulent, and since the orally ingested poly-unsaturated fatty acid and/or biotin are less decomposed and less assimilated in the intestine and more effectively absorbed in the intestine, improvement in metabolism of fatty acids produces prophylactic and therapeutic effects against dermatosis, etc.

The present invention is described in the following Examples, Reference Examples and Experimental Examples.

Example 1

A 420 g portion of flaky LINOX (product of Idemitsu Petrochemical Co.: dried cells of Mucor bacteria containing 10% γ-linolenic acid; and the same product was used in the Examples hereinafter) was finely divided in a mortar to less than 100 mesh. To the resulting granules were added 80 g of ROVIMIX H-2 (product of Nihon Roche Co.; biotin content 2%; and the same product was used in the Examples hereinafter) which had been passed through a 100 mesh sieve and 500 g of KOROLAC D (product of Nisshin Flour Milling Co.; containing $10^9$ cells or more of Bifidobacterium pseudolongum SS-24 strain per 1 gram of the product; and the same product was used in the Examples hereinafter), and the mixture was thoroughly mixed with a rocking mixer to obtain the prescription diet composition of the present invention.

Example 2

An 80 g portion of ROVIMIX H-2 which had been passed through a 100 mesh sieve, 500 g of KOROLAC D and 420 g of lactose (product of Megure Co.; the same product was used in the Examples hereinafter) were adequately mixed together with a rocking mixer to obtain the prescription diet composition of the present invention.

Example 3

The prescription diet composition was prepared by the same method as described in Example 1, except that 420 g of α-linolenic acid powder (cyclodextrin clathrate powder containing 20% α-linolenic acid) produced according to the method described in Japanese Published Unexamined Patent Application No. 41395/84 was used instead of LINOX.

Example 4

The prescription diet composition was prepared by the same method as described in Example 1, except that 420 g of DHA powder (cyclodextrin clathrate powder containing 14% DHA) produced according to the method described in Japanese Published Unexamined Patent Application No. 41395/84 was used instead of LINOX.

Example 5

The prescription diet composition was prepared by the same method as described in Example 1, except that 500 g of "Biofermin for animals" (product of Biofermin Seiyaku Co.; $10^9$ cells of *Streptococcus fecalis* and $10^9$ cells of *Lactobacillus acidophilus* per 10 g) was used instead of KOROLAC D.

Example 6

The prescription diet composition was prepared by the same method as described in Example 1, except that 500 g of "Miyari cell powder for incorporation" (product of Miyarisan Co.; containing 30 mg of *Clostridium butyricum* per 1 gram of the product) was used instead of KOROLAC D.

Reference Example 1

A 420 g portion of flaky LINOX was finely divided in a mortar to less than 100 mesh. To the resulting granules were added 80 g of ROVIMIX H-2 which had been passed through a 100 mesh sieve and 500 g of lactose and the mixture was thoroughly mixed with a rocking mixer to obtain a composition.

Reference Example 2

An 80g portion of ROVIMIX H-2 which had been passed through a 100 mesh sieve and 920 g of lactose were adequately mixed with a rocking mixer, to obtain a composition.

Reference Example 3

A 0.8 g portion of ROVIMIX H-2 which had been passed through a 100 mesh sieve and 999.2 g of lactose were adequately mixed with a rocking mixer, to obtain a composition.

Reference Example 4

A 500 g portion of KOROLAC D which had been passed through a 100 mesh sieve and 500 g of lactose were adequately mixed with a rocking mixer, to obtain a composition.

Experimental Example 1 Prophylactic effect in dogs

Eighteen household-bred dogs having a body weight of 5.0±1.0 kg and with a history of dermatosis were arbitrarily selected and divided into 3 groups, A, B and C, each consisting of 6 dogs. Dog food was mixed with the following three types of the composition so as to provide a daily intake of 0.1 g per 1 kg of body weight; the composition obtained in Example 1 for group A, the composition obtained in Reference Example 1 for group B, and lactose alone for group C. The dogs were fed three times a day. Each of the components in 1 gram of the composition given to each group is identified in Table 1.

The above experiment was conducted over a 2 month period, during which the condition of the skin was observed on the basis of the evidence of itching, redness, eczema, alopecia and crusts. The results are shown in Table 2.

TABLE 1

| Each component in 1 gram of the composition given to each group (mg) | | | |
|---|---|---|---|
| | Group A | Group B | Group C |
| γ-linolenic acid | 42 | 42 | 0 |
| Biotin | 1.6 | 1.6 | 0 |
| KOROLAC D | 500 | 0 | 0 |
| Lactose | 0 | 500 | 1000 |

TABLE 2

| Number of dogs suffering from dermatosis | | | |
|---|---|---|---|
| | Group A | Group B | Group C |
| Number of dogs | 1 | 4 | 6 |

As shown in Table 2, dermatosis can be prevented by feeding the dog food containing the composition of the present invention to dogs.

Experimental Example 2 Prophylactic effect in dogs

Six household-bred dogs having a body weight of 5.0±1.0 kg and with a history of dermatosis were arbitrarily selected. Separately from dog food, the composition obtained in Example 1 was ingested once a day, in an amount of 0.1 g per 1 kg of body weight.

The experiment was conducted over a 2 month period, during which the condition of the skin was observed on the basis of the evidence of itching, redness, eczema, alopecia and crusts. It was observed that dermatosis occurred in only 2 dogs.

Experimental Example 3 Prophylactic effect in cats

Eighteen household-bred cats having a body weight of 3.5±1.0 kg and with a history of dermatosis were arbitrarily selected and divided into 3 groups, A, B and C, each consisting of 6 cats. Cat food was mixed with the following three types of the composition so as to provide a daily intake of 0.1 g per 1 kg of body weight; the composition obtained in Example 1 for group A, the composition obtained in Reference Example 1 for group B, and lactose alone for group C. The cats were fed three times a day. Each of the components in 1 gram of the composition given to each group was the same as in Table 1.

The above experiment was conducted over a 2 month period, during which the condition of the skin was observed on the basis of the evidence of itching, redness, eczema, alopecia and crusts. The results are shown in Table 3.

TABLE 3

| Number of cats suffering from dermatosis | | | |
|---|---|---|---|
| | Group A | Group B | Group C |
| Number of cats | 0 | 4 | 6 |

As shown in Table 3, dermatosis can be prevented by feeding the cat food containing the composition of the present invention to cats.

Experimental Example 4 Prophylactic effect in cats

Six household-bred cats having a body weight of 3.5±1.0 kg and with a history of dermatosis were arbitrarily selected.

Separately from cat food, the composition obtained in Example 1 was ingested once a day, in an amount of 0.1 g per 1 kg of body weight.

The experiment was conducted over a 2 month period, during which the condition of the skin was observed on the basis of the evidence of itching, redness, eczema, alopecia and crusts. It was observed that dermatosis occurred in only 1 cat.

Experimental Example 5

Therapeutic effect in cats (effect when used in combination with an antipruritic agent)

Fifteen cats having a body weight of 3.5±1.0 kg and suffering from eczema such as redness, etc. were divided into 5 groups, A, B, C, D and E, each consisting of 3 cats. Separately from cat food, the following three types of the composition were ingested once a day over a period of 10 days, in an amount of 0.3 g per 1 kg of body weight, the composition obtained in Example 1 to groups A and D, the composition obtained in Reference Example 1 to group B, and lactose alone to groups C and E. The condition of the skin was observed. Prednisolone ("Prednisolone injection", product of Fujita Seiyaku Co.), which was a dermatotherapeutic medicine was subcutaneously injected once a day to groups D and E in an amount of 0.4 mg/kg body weight. Each of the components in 1 gram of the composition given to each group is shown in Table 4.

TABLE 4

Each component in 1 gram of the composition (mg)

| | Group A | Group B | Group C | Group D* | Group E* |
|---|---|---|---|---|---|
| γ-linolenic acid | 42 | 42 | 0 | 42 | 0 |
| Biotin | 1.6 | 1.6 | 0 | 1.6 | 0 |
| KOROLAC D | 500 | 0 | 0 | 500 | 0 |
| Lactose | 0 | 500 | 1000 | 0 | 1000 |

Note: The "*" denotes the groups having simultaneous administration of prednisolone.

The symptoms on the 3rd, 7th and 10th day from the initial administration of prednisolone were determined for each cat on the basis of the score shown in Table 5. The average scores were obtained for each group, and shown in Table 6.

TABLE 5

Score for determination of skin symptoms

| Skin symptoms | Scale |
|---|---|
| Completely cured | 3 |
| Considerably cured | 2 |
| Somewhat cured | 1 |
| Remained unchanged | 0 |
| Somewhat worse | −1 |
| Considerably worse | −2 |
| Extremely worse | −3 |

TABLE 6

Determination of skin symptoms

| | Group A | Group B | Group C | Group D | Group E |
|---|---|---|---|---|---|
| 3rd day | 0.3 | 0 | −1.3 | 1.0 | 0.7 |
| 7th day | 1.0 | 0.7 | −3.0 | 3.0 | 1.7 |
| 10th day | 2.0 | 0.7 | NT | NT | 2.0 |

Note: NT: not tested
(1) The skin symptoms in three cats of Group C got worse on the 7th day from the initial administration, and therefore the test was suspended.
(2) The skin in all 3 cats of Group D was completely recovered on the 7th day from the initial administration, and therefore the test was suspended.

As shown in Table 6, dermatosis is treated by having cats ingest the prescription diet composition of the present invention, and the therapeutic effect is enhanced when it is used in combination with a dermatotherapeutic medicine. It is possible to reduce the dosage of the dermatotherapeutic medicine, and thus to minimize the occurrence of side effects due to the dermatotherapeutic medicine.

Experimental Example 6 Therapeutic effect in dogs

Ten dogs having a body weight of 10.0±1.0 kg and suffering from slight eczema such as redness, etc. were divided into 5 Groups, A, B, C, D and E, each consisting of 2 dogs. Separately from dog food, the three types of the composition were ingested once a day over a period of 14 days, in an amount of 0.25 g per 1 kg of body weight. The composition obtained in Example 2 to Group A, the compositions obtained in Reference Examples 2, 3 and 4 to Groups B, C and D, respectively, and lactose alone to Group E. The condition of the skin was observed. Each of the components in 1 gram of the composition given to each group is shown in Table 7.

TABLE 7

Each component in 1 gram of the composition (mg)

| | Group A | Group B | Group C | Group D | Group E |
|---|---|---|---|---|---|
| Biotin | 1.6 | 1.6 | 0.016 | 0 | 0 |
| KOROLAC D | 500 | 0 | 0 | 500 | 0 |
| Lactose | 429 | 920 | 999.2 | 500 | 1000 |

The symptoms on the 3rd, 7th and 14th day were determined for each dog on the basis of the score shown in Table 5. The average scores were obtained for each group, and shown in Table 8.

TABLE 8

Determination of skin symptoms

| | Group A | Group B | Group C | Group D | Group E |
|---|---|---|---|---|---|
| 3rd day | 0.5 | 0 | −1.0 | −0.5 | −1.0 |
| 7th day | 1.0 | 0.5 | −2.5 | −1.5 | −2.5 |
| 14th day | 1.5 | 0.5 | NT | NT | NT |

Note: (1) NT: not tested
The skin symptoms in the dogs of Groups C, D and E got worse on the 7th day from the initial intake, and therefore the test was suspended.

As shown in Table 8, the composition of the present invention exhibited a more notable therapeutic effect against dermatosis than the compositions containing biotin or bifidobacteria alone.

Experimental Example 7 Therapeutic effect in dogs

To a Shih Tzu dog (3 years old, female, body weight 5.5 kg) suffering with eczema and pruritus in the tail head and pubic regions due to flea parasites, 1.25 mg of prednisolone was orally administered twice a day over a period of 5 days, separately from dog food. The skin symptoms were not alleviated, and deposition of a light pigment was also observed in the pubic region.

The dog was subjected to once-a-day intake of 0.55 g of the composition obtained in Example 1, while orally administering 1.25 mg of prednisolone twice a day. The pruritus, eczema and pigment disappeared on the 3rd day from the initial intake of the composition.

Experimental Example 8 Therapeutic effect in dogs

To an Akita dog (3 years old, male, body weight 33.0 kg) emitting a foul odor due to inflammation and purulence of the external auditory canal of the left ear, four tablets of Jumihaijo (product of Shinwa Seiyaku Co.) was orally administered once a day, and also 6.6 g of the composition obtained in Example 1 was ingested once a day, separately from dog food. The diseased part was dried and healed on the 3rd day from the initial intake of the composition.

Experimental Example 9 Therapeutic effect in cats

To a Japanese cat (10 years old, male, body weight 4.7 kg) suffering with crusts, pruritus, inflammation, alopecia on the left hind leg, and eczema of the dorsum, 4.7 mg of prednisolone and 118 mg of chloromycetin were subcutaneously injected once a day and also 1.4 g of the composition obtained in Example 1 was ingested once a day, separately from cat food. On the 7th day from the initial intake, the dorsal eczema was still slightly observed, and the prurintus and inflammation had disappeared.

Experimental Example 10 Therapeutic effect of the α-linolenic acid-containing composition in dogs By a Shih Tzu dog (3 years old, male, body weight 4.9 kg) suffering with slight eczema including redness in the tail head region, 0.5 g of the composition obtained in Example 3 was ingested twice a day, separately from dog food. On the 10th day from the initial intake, the diseased part healed.

Experimental Example 11 Therapeutic effect of the DHA-containing composition in cats By a Japanese cat (9 years old, female, body weight 4.9 kg) suffering with slight eczema including redness in the dorsal region, 0.5g of the composition obtained in Example 4 was ingested twice a day, separately from cat food. On the 10th day from the initial intake of the composition, the diseased part healed.

Experimental Example 12 Therapeutic effect of the lactic acid bacteria containing composition in dog A Shih Tzu dog (4 years old, male, body weight 6.0 kg) suffering from slight eczema including redness in the tail head region, ingested twice a day 0.5 g of the composition obtained in Example 5, separately from dog food. On the 7th day from the initial intake of the composition, the diseased part healed.

Experimental Example 13 Therapeutic effect of the butyric acid bacteria containing composition in dogs A Shih Tzu dog (3 years old, male, body weight 5.5 kg) suffering with slight eczema including redness in the tail head region ingested twice a day 0.5 g of the composition obtained in Example 6, separately from dog food. On the 7th day from the initial intake of the composition, the diseased part healed.

What is claimed is:

1. A prescription diet composition for a pet animal, which comprises:

(i) untreated or treated cells of bacteria being selected from the group consisting of lactic acid bacteria, Bifidobacterium, butyric acid bacteria and Bacillus, said treated cells being selected from the group consisting of washed cells, dry cells, freezed cells, freeze-dried cells, acetone-dried cells, organic solvent-treated cells, ultrasonically treated cells, and mechanically disrupted cells; and (ii) at least one of poly-unsaturated fatty acid being selected form the group consisting of γ-linolenic acid, α-linolenic acid, eicosapentanoic acid and docosahexaenoic acid, and (iii) biotin.

2. A method for prophylactic or therapeutic treatment of dermatosis in a pet animal, which comprises feeding the pet animal an anti-dermatosis effective amount of the prescription diet composition of claim 1.

3. The method according to claim 2, wherein the anti-dermatosis effective amount of the prescription diet composition per animal per day is, 0.1 g–2.5 g for pet animals having a body weight of less than 5 kg, 0.2 g–5.0 g for pet animals having a body weight of 5 kg or between 5 and 10 kg, 0.3 g–7.5 g for pet animals having a body weight of 10 kg or between 10 and 15 kg, and 0.5 g–20 g for pet animals having a body weight of about 15 kg.

4. A prescription diet composition for a dog, which comprises:

(i) untreated or treated cells of bacteria being selected from the group consisting of lactic acid bacteria, Bifidobacterium, butyric acid bacteria and Bacillus, said treated cells being selected from the group consisting of washed cells, dry cells, freezed cells, freeze-dried cells, acetone-dried cells, organic solvent-treated cells, ultrasonically treated cells, and mechanically disrupted cells; and (ii) biotin.

5. A method for prophylactic or therapeutic treatment of dermatosis in a dog, which comprises feeding the dog an anti-dermatosis effective amount of the prescription diet composition of claim 4.

6. A prescription diet composition for a dog or cat which comprises an anti-dermatosis effective amount of γ-linolenic acid, untreated or treated cells of bacteria selected from the group consisting of lactic acid bacteria, Bifidobacterium, butyric acid bacteria and Bacillus, said treated cells selected from the group consisting of washed cells, dry cells, freezed cells, freeze-dried cells, acetone-dried cells, organic solvent-treated cells, ultrasonically treated cells or mechanically disrupted cells thereof, and biotin.

7. A method for the prophylactic or therapeutic treatment of dermatosis in a dog or cat, which comprises feeding the dog or cat the prescription diet composition of claim 6.

8. A prescription diet composition for a pet animal, which comprises an antiflatulent which is selected from the group consisting of lactic acid bacteria, Bifidobacterium, butyric acid bacteria, Bacillus and washed cells, dry cells, freezed cells, freeze-dried cells, acetone-dried cells, organic solvent-treated cells, ultrasonically treated cells, and mechanically disrupted cells of said bacteria; and at least one of poly-unsaturated fatty acid being selected from an ω3 or ω6 essential fatty acid, and biotin.

* * * * *